(12) United States Patent
Owen et al.

(10) Patent No.: US 7,892,743 B2
(45) Date of Patent: *Feb. 22, 2011

(54) SUBTRACTIVE SINGLE LABEL COMPARATIVE HYBRIDIZATION

(75) Inventors: Renius X. Owen, Lake Elsinore, CA (US); Charles M. Strom, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/392,951

(22) Filed: Feb. 25, 2009

(65) Prior Publication Data

US 2009/0155809 A1 Jun. 18, 2009

Related U.S. Application Data

(63) Continuation of application No. 11/830,768, filed on Jul. 30, 2007, now Pat. No. 7,507,539.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search ............ 435/6; 536/23.1, 24.3
See application file for complete search history.

(56) References Cited

U.S. PATENT DOCUMENTS

| | | | |
|---|---|---|---|
| 4,775,619 A | 10/1988 | Urdea | |
| 5,135,717 A | 8/1992 | Renzoni et al. | |
| 5,143,854 A | 9/1992 | Pirrung et al. | |
| 5,175,270 A | 12/1992 | Niilsen et al. | |
| 5,324,633 A | 6/1994 | Fodor et al. | |
| 5,387,617 A | 2/1995 | Hedstrand et al. | |
| 5,393,795 A | 2/1995 | Hedstrand et al. | |
| 5,434,049 A | 7/1995 | Okano et al. | |
| 5,484,904 A | 1/1996 | Nilsen et al. | |
| 5,487,973 A | 1/1996 | Nilsen et al. | |
| 5,530,092 A | 6/1996 | Meijer et al. | |
| 5,539,517 A | 7/1996 | Cabib et al. | |
| 5,556,752 A | 9/1996 | Lockhart et al. | |
| 5,560,929 A | 10/1996 | Hedstrand et al. | |
| 5,578,832 A | 11/1996 | Trulson et al. | |
| 5,580,990 A | 12/1996 | van den Berg et al. | |
| 5,632,957 A | 5/1997 | Heller et al. | |
| 5,635,351 A | 6/1997 | Feuerstein et al. | |
| 5,652,099 A | 7/1997 | Conrad | |
| 5,665,549 A | 9/1997 | Pinkel et al. | |
| 5,700,637 A | 12/1997 | Southern | |
| 5,714,327 A | 2/1998 | Houthoff et al. | |
| 5,721,098 A | 2/1998 | Pinkel et al. | |
| 5,744,305 A | 4/1998 | Fodor et al. | |
| 5,770,456 A | 6/1998 | Holmes | |
| 5,790,727 A | 8/1998 | Dhadwal et al. | |
| 5,800,992 A | 9/1998 | Fodor et al. | |
| 5,807,522 A | 9/1998 | Brown et al. | |
| 5,830,645 A | 11/1998 | Pinkel et al. | |
| 5,847,708 A | 12/1998 | Wolff | |
| 5,856,097 A | 1/1999 | Pinkel et al. | |
| 5,856,174 A | 1/1999 | Lipshutz et al. | |
| 5,863,504 A | 1/1999 | Heffelfinger et al. | |
| 5,880,473 A | 3/1999 | Ginestet | |
| 5,922,617 A | 7/1999 | Wang et al. | |
| 5,943,129 A | 8/1999 | Hoyt et al. | |
| 5,959,098 A | 9/1999 | Goldberg et al. | |
| 5,965,362 A | 10/1999 | Pinkel et al. | |
| 5,965,452 A | 10/1999 | Kovacs | |
| 5,976,790 A | 11/1999 | Pinkel et al. | |

(Continued)

FOREIGN PATENT DOCUMENTS

EP 0 539 466 11/1996

(Continued)

OTHER PUBLICATIONS

Antony et al., A Molecular Beacon Strategy for the Thermodynamic Characterization of Triplex DNA: Triplex Formation at the Promotion Region of Cyclin D1, *Biochemistry*, 40:9387-9395 (2001).

(Continued)

*Primary Examiner*—Ethan Whisenant
(74) *Attorney, Agent, or Firm*—Foley & Lardner LLP

(57) ABSTRACT

Provided are methods of determining differences between nucleic acids in a test sample and a reference sample. In certain embodiments the methods are used for detecting and mapping chromosomal or genetic abnormalities associated with various diseases or with predisposition to various diseases, or to detecting the phenomena of large scale copy number variants. In particular, provided are advanced methods of performing array-based comparative hybridization that allow reproducibility between samples and enhanced sensitivity by using the same detectable label for both test sample and reference sample nucleic acids. Invention methods are useful for the detection or diagnosis of particular disease conditions such as cancer, and detecting predisposition to cancer based on detection of chromosomal or genetic abnormalities and gene expression level. Invention methods are also useful for the detection or diagnosis of hereditary genetic disorders or predisposition thereto, especially in pre-natal samples. Moreover, invention methods are also useful for the detection or diagnosis of de novo genetic aberrations associated with post-natal developmental abnormalities.

20 Claims, No Drawings

U.S. PATENT DOCUMENTS

| | | | |
|---|---|---|---|
| 5,985,566 | A | 11/1999 | Houthoff et al. |
| 6,013,440 | A | 1/2000 | Lipzhutz et al. |
| 6,022,963 | A | 2/2000 | McGall et al. |
| 6,045,996 | A | 4/2000 | Cronin et al. |
| 6,048,695 | A | 4/2000 | Bradley et al. |
| 6,049,380 | A | 4/2000 | Goodwin et al. |
| 6,054,270 | A | 4/2000 | Southern |
| 6,054,279 | A | 4/2000 | Nadeau et al. |
| 6,055,325 | A | 4/2000 | Garini et al. |
| 6,063,338 | A | 5/2000 | Pham et al. |
| 6,066,459 | A | 5/2000 | Garini et al. |
| 6,140,044 | A | 10/2000 | Besemer et al. |
| 6,143,495 | A | 11/2000 | Lizardi et al. |
| 6,159,685 | A | 12/2000 | Pinkel et al. |
| 6,191,425 | B1 | 2/2001 | Imai |
| 6,197,501 | B1 | 3/2001 | Cremer et al. |
| 6,235,504 | B1 | 5/2001 | Zhang et al. |
| 6,252,664 | B1 | 6/2001 | Barberá-Guillem |
| 6,258,606 | B1 | 7/2001 | Kovacs |
| 6,261,776 | B1 | 7/2001 | Pirrung et al. |
| 6,268,132 | B1 | 7/2001 | Conrad |
| 6,277,489 | B1 | 8/2001 | Abbott et al. |
| 6,277,581 | B1 | 8/2001 | O'Brien et al. |
| 6,277,628 | B1 | 8/2001 | Johann et al. |
| 6,294,331 | B1 | 9/2001 | Ried et al. |
| 6,514,700 | B1 | 2/2003 | Singh |
| 2001/0007747 | A1 | 7/2001 | Bochkariov et al. |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0014449 | A1 | 8/2001 | Nerenberg et al. |
| 2001/0016322 | A1 | 8/2001 | Caren et al. |
| 2001/0018514 | A1 | 8/2001 | McGall et al. |
| 2001/0018642 | A1 | 8/2001 | Balaban et al. |
| 2001/0019827 | A1 | 9/2001 | Dawson et al. |
| 2002/0068293 | A1 | 6/2002 | Delenstarr et al. |
| 2002/0115841 | A1 | 8/2002 | Brown et al. |
| 2003/0104395 | A1* | 6/2003 | McLaughlin et al. ............ 435/6 |
| 2004/0053275 | A1 | 3/2004 | Shafer |
| 2004/0094930 | A1 | 5/2004 | Machado |
| 2005/0260665 | A1 | 11/2005 | Mohammed et al. |
| 2006/0263811 | A1* | 11/2006 | Jeon et al. ........................ 435/6 |
| 2007/0122820 | A1 | 5/2007 | Mohammed |

FOREIGN PATENT DOCUMENTS

| | | |
|---|---|---|
| EP | 0539466 | 11/1996 |
| WO | WO 93/18186 | 9/1993 |
| WO | WO 96/17958 | 6/1996 |
| WO | WO 97/46313 | 12/1997 |
| WO | WO 99/09217 | 2/1999 |
| WO | WO 99/51773 | 10/1999 |
| WO | WO 99/60163 | 11/1999 |
| WO | WO 00/09650 | 2/2000 |
| WO | WO 00/26412 | 5/2000 |
| WO | WO 00/42222 | 7/2000 |
| WO | WO 00/47600 | 8/2000 |
| WO | WO 01/01144 | 1/2001 |
| WO | WO 01/46467 | 6/2001 |
| WO | WO-01/87348 | 11/2001 |
| WO | WO 02/061140 | 8/2002 |
| WO | WO 03/012147 | 2/2003 |
| WO | WO 03/020898 | 3/2003 |

OTHER PUBLICATIONS

Bai et al., Photocleavage of a 2-nitrobenzyl linker bridging a fluorophore to the 5' end of DNA, *Proc. Natl. Acad. Sci.*, 100:409-413, (2003).

Bischoff et al., Introduction of 5'-Terminal Functional Groups into Synthetic Oligonucleotides for Selective Immobilization, *Anal. Biochem.*, 164:336-344, (1987).

Bowtell, David, D. L., Options available—from start to finish—for obtaining expression data by microarray, *Nature Genetics*, Supp. 21:25-32, (1999).

Cheung et al., Integration of cytogenetic landmarks into the draft sequence of the human genome, *Nature* 409:953-958, (2001).

Chu et al., Low fluorescence background electroblotting membrane for DNA sequencing, *Electrophoresis*, 13:105-114, (1992).

Diago et al., Degenerate Oligonucleotide Primed-Polymerase Chain Reaction-Based Array Comparative Genomic Hybridization for Extensive Amplicon Profiling of Breast Cancers, A New Approach for the Molecular Analysis of Paraffin-Embedded Cancer Tissue, *Am. J. Pathol.*, 158:1623-1631, (2001).

Hamaguchi et al., Aptamer Beacons for the Direct Detection of Proteins, *Anal. Biochem*. 294:126-131, (2001).

Henegariu et al., Custom fluorescent-nucleotide synthesis as an alternative method for nucleic acid labeling, *Nat. Biotechnol*. 18:345-348, (2000).

Jain, K.K., Applications of biochip and microarray systems in pharmacogenomics, *Pharmacogenomics* 1:289-307, (2000).

Jameson, D.M., and Eccleston, John F., Fluorescent Nucleotide Analogs: Synthesis and Applications, *Meth. Enzymol*, 278:363-390, (1997).

Johnston, Mark, Gene chips: Array of hope for understanding gene regulation, *Curr. Biol.*, 8:R171-R174, (1998).

Kaboev et al., PCR hot start using primers with the structure of molecular beacons (hairpin-like structure), *Nucl. Acids Res*. 28:E94, (2000).

Kallioniemi et al., Comparative Genomic Hybridization for Molecular Cytogenetic analysis of Solid Tumors, Science 258:818-821, (1992).

Kern, Suzanne, and Hampton, Garret M., Direct Hybridization of Large-Insert Genomic Clones on High-Density Gridded cDNA Filter Arrays, Biotechniques, 23:120-124, (1997).

Klinger et al., Rapid Detection of Chromosome Aneuploidies in Uncultured Amniocytes by Using Fluorescence in Situ Hybridization (FISH), *Am. J. Hum. Genet*. 51:52-65, (1992).

Kremsky et al., Immobilization of DNA via oligonucleotides containing an aldehyde or carboxylic acid group at the 5' terminus, *Nucl. Acids Res*. 15:2891-2910, (1987).

Mansfield et al., Nucleic acid detection using non-radioactive labelling methods, *Mol Cell. Probes* 9:145-156, (1995).

McPherson et al., A physical map of the human genome, *Nature* 409:934-41, (2001).

Nielsen et al., Peptide nucleic acids (PNAs): Potential anti-sense and anti-gene agents, *Anticancer Drug Des*. 8:53 63, (1993).

Poddar, S.K. and Le, C.T., *Bordetella pertussis* detection by spectrofluorometry using polymerase chain reaction (PCR) and a molecular beacon probe, *Mol. Cell. Probes* 15:161-167, (2001).

Schummer et al., Inexpensive Handheld Device for the Construction of High-Density Nucleic Acid Arrays, *Biotechniques* 23:1087-1092, (1997).

Smirnov, Ivan and Shafer, Richard H., Effect of Loop Sequence and Size on DNA Aptamer Stability, *Biochemistry* 39:1462-1468, (2000).

Smith et al., Direct Mechanical Measurements of the Elasticity of Single DNA Molecules by Using Magnetic Beads, *Science* 258:1122-1126, (1992).

Sokol et al., Real time detection of DNA-RNA hybridization in living cells, *Proc. Natl. Acad. Sci. USA* 95:11538-11543, (1998).

Solinas-Toldo et al., Matrix-Based Comparative Genomic Hybridization: Biochips to Screen for Genomic Imbalances, *Genes, Chromosomes & Cancer* 20:399-407, (1997).

Theillet, Le typage genomique: de la cytogenetique moleculaire aux puces a ADN. *Bull. Cancer* 88:261-268, 2001 (An abstract in English is on front page of article).

Werner, Thomas, Cluster analysis and promoter modelling as bioinformatics tools for the identification of target genes from expression array data, *Pharmacogenomics* 2:25-36, (2001).

Wittrup et al., Fluorescence Array Detector for Large-Field Quantitative Fluorescence Cytometry, Cytometry 16:206-213, (1994).

Yamamoto, Rika and Kumar, Penmetcha K.R., Molecular beacon aptamer fluoresces in the presence of Tat protein of HIV-1, *Genes Cells* 5:389-396, (2000).

Zhu et al., Directly labeled DNA probes using fluorescent nucleotides with different length linkers, *Nucl. Acids Res.* 22:3418-3422, (1994).

Schena et al., Parallel human genome analysis: Microarray-based expression monitoring of 1000 genes. Proceedings of the National Academy of Science, 93:10614-10619, 1996.

Sehgal et al., Application of the differential hybridization of Atlas™ human expression arrays technique in the identification of differentially expressed genes in human glioblastoma multiforme tumor tissue, Journal of Surgical Oncology, 67:234-241, 1998.

Taton et al., Journal of the American Chemical Society, 21: 5164-5165, 2001.

Ramakrishnan et al., An assessment on Motorola CodeLink™ microarray performance for gene expression profiling applications. Nucleic Acids Research, 30(7): 1-12, 2002 XP-002962789.

Armstrong et al., Suspension arrays for high throughput, multiplexed single nucleotide polymorphism genotyping. Cytometry, 40:102-108, 2000.

Supplementary European Search Report for EPO Patent Application No. EP 05 75 2947.

Allawi et al., Thermodynamics and NMR of Internal G T Mismatches in DNA, Biochemistry, 36:10581-10594, 1997.

Notice of Allowance dated Nov. 13, 2008 for U.S. Appl. No. 11/830,768.

Office Action Jun. 27, 2007 for U.S. Appl. No. 11/134,133.

Office Action dated Apr. 14, 2009 for U.S. Appl. No. 11/134,133.

Office Action dated Aug. 1, 2008 for U.S. Appl. No. 11/830,768.

Office Action dated Jan. 21, 2010 for U.S. Appl. No. 11/134,133.

Communication dated Jul. 12, 2010 in related EP application 05752947.

International Preliminary Report on Patentability dated Feb. 20, 2007 in related application PCT/US2005/017986.

International Search Report dated Jan. 29, 2007 in related application PCT/US2005/017986.

US Office Action dated Aug. 7, 2008 in related U.S. Appl. No. 11/137,133.

\* cited by examiner

SUBTRACTIVE SINGLE LABEL COMPARATIVE HYBRIDIZATION

FIELD OF THE INVENTION

The present invention relates to the detection and mapping of chromosomal or genetic abnormalities, including those associated with various diseases or with predisposition to various diseases. In a particular aspect, the present invention relates to the use of nucleic acids in comparative hybridization.

BACKGROUND OF THE INVENTION

The following description is provided to assist the understanding of the reader. None of the information provided or references cited is admitted to be prior art to the present invention.

Comparative hybridization methods test the ability of two nucleic acids to interact with a third target nucleic acid. In particular, comparative genomic hybridization (CGH) is a method for detecting chromosomal abnormalities. CGH was originally developed to detect and identify the location of gain or loss of DNA sequences, such as deletions, duplications or amplifications commonly seen in tumors (Kallioniemi et al., Science 258:818-821, 1992). For example, genetic changes resulting in an abnormal number of one or more chromosomes (i.e., aneuploidy) have provided useful diagnostic indicators of human disease, specifically as cancer markers. Changes in chromosomal copy number are found in nearly all major human tumor types. For a review, see Mittelman et al., "Catalog of Chromosome Aberrations" in $Cancer$, Vol. 2 (Wiley-Liss, 1994).

In addition, the presence of aneuploid cells has also been used as a marker for genetic chromosal abnormalities. Various chromosomal abnormalities may occur in an estimated 0.5% of all live births. For example, Down's syndrome or trisomy 18 which has an incidence of about 1 in 800 live births, is commonly the subject of a variety of prenatal screens or diagnostic techniques. Chromosomal aneuploidies involving chromosomes 13, 18, 21, X and Y account for up to 95% of all liveborn chromosomal aberrations resulting in birth defects (Whiteman et al., Am. J. Hum. Genet. 49:A127-129, 1991), and up to 67% of all chromosomal abnormalities, including balanced translocations (Klinger et al., Am. J. Hum. Genet. 51:52-65, 1992).

CGH is useful to discover and map the location of genomic sequences with variant copy number without prior knowledge of the sequences. Oligonucleotide probes directed to known mutations are not required for CGH. Early CGH techniques employ a competitive in situ hybridization between test DNA and normal reference DNA, each labeled with a different color, and a metaphase chromosomal spread. Chromosomal regions in the test DNA, which are at increased or decreased copy number as compared to the normal reference DNA can be quickly identified by detecting regions where the ratio of signal from the two different colors is altered. For example, those genomic regions that have been decreased in copy number in the test cells will show relatively lower signal from the test DNA than the reference (compared to other regions of the genome (e.g., a deletion)); while regions that have been increased in copy number in the test cells will show relatively higher signal from the test DNA (e.g., a duplication). Where a decrease or an increase in copy number is limited to the loss or gain of one copy of a sequence, CGH resolution is usually about 5-10 Megabases (Mb).

CGH has more recently been adapted to analyze individual genomic nucleic acid sequences rather than a metaphase chromosomal spread. Individual nucleic acid sequences are arrayed on a solid support, and the sequences can represent the entirety of one or more chromosomes, or the entire genome. The hybridization of the labeled nucleic acids to the array targets is detected using different labels, e.g., two color fluorescence. Thus, array-based CGH with a plurality of individual nucleic acid sequences allows one to gain more specific information than a chromosomal spread, is potentially more sensitive, and facilitates the analysis of samples.

For example, in a typical array-based CGH, equal amounts of total genomic nucleic acid from cells of a test sample and a normal reference sample are labeled with two different colors of fluorescent dye and co-hybridized to an array of BACs, which contain the cloned nucleic acid fragments that collectively cover the cell's genome. The resulting co-hybridization produces a fluorescently labeled array, the coloration of which reflects the competitive hybridization of sequences in the test and reference genomic DNAs to the homologous sequences within the arrayed BACs. Theoretically, the copy number ratio of homologous sequences in the test and reference genomic nucleic acid samples should be directly proportional to the ratio of their respective colored fluorescent signal intensities at discrete BACs within the array. Array-based CGH is described in U.S. Pat. Nos. 5,830,645 and 6,562,565 for example, using target nucleic acids immobilized on a solid support in lieu of a metaphase chromosomal spread.

When combining more than one color or type of labeled nucleic acid in a hybridization mixture, the relative concentrations and/or labeling densities may be adjusted for various purposes. Adjustments may be made by selecting appropriate detection reagents (avidin, antibodies and the like), or by the design of the microscope filters among other parameters. When using quantitative image analysis, mathematical normalization can be used to compensate for general differences in the staining intensities of different colors. Thus, the use of different labels to distinguish test from reference genomic nucleic acids in traditional CGH entails additional refinements or adjustments that complicate sample processing, standardization across samples, and evaluation of the results obtained. For example, when using visual observation or photography of the results, the individual color intensities need to be adjusted for optimum observability of changes in their relative intensities.

U.S. Patent Application Publication Number 2005/0260665, (hereinafter "the '665 application") which is hereby incorporated by reference herein in its entirety including all figures and tables, discloses single-label CGH methods.

One approach of the single label CGH methods disclosed in the '665 application is referred to as an "additive" approach. In this approach, the test sample nucleic acids comprise a first tag; and the reference sample nucleic acids comprise a second tag. Following hybridization, the surface is contacted with a first complex containing a detectable label and a first entity, such that the first complex selectively binds with the first tag. The next step comprises determining the location and amount of the detectable label bound to the array surface (i.e., to "read" the array). Once the array is read to determine the amount of detectable label associated with nucleic acid that comprises the first tag, the surface is then contacted with a second complex containing the same detectable label as present in the first complex and containing a second entity, such that the second complex selectively binds with the second tag. The array is then read a second time to determine the location and amount of the total detectable label representing both nucleic acids hybridized to the surface. The last step comprises using the results of the two reads to determine the amount of the hybridized nucleic acid that is associated with the second tag.

A second approach of the single label CGH methods disclosed in the '665 application is referred to as an "subtractive" approach. In the "subtractive" approach, the linkage used to attach the detectable label to the test nucleic acid and the reference nucleic acid is different, allowing for selective cleavage or removal of one linkage over that of the other. As a first step, the total detectable signal on the array, which represents label linked to both the test sample and the reference sample nucleic acids hybridized to the array, is first positionally quantified. The array is then subjected to a condition or treatment that causes selective cleavage of the linker such that the label is stripped from either the hybridized test or reference nucleic acids, whichever has the susceptible linkage. The remaining signal representing nucleic acid that is not linked to the susceptible linker is then positionally quantified. The next step includes using the results of the two reads to determine the amount of the hybridized nucleic acid that is attached to the label via the susceptible linkage. In a preferred approach, the signal representing the nucleic acid that is linked to the label by the susceptible linker is determined by subtracting the remaining signal following selective removal from the total signal. The signal from the two samples thus determined can be used to identify differences between the test sample genomic nucleic acids and the reference sample genomic nucleic acids so as to detect chromosomal or genetic abnormalities associated with the test sample nucleic acid.

As described below, improvements in comparative hybridization methods including CGH are provided. In particular, provided are improved methods that are variations of the "subtractive" methods disclosed in the '665 application.

SUMMARY OF THE INVENTION

The present invention overcomes the limitations of using different labels in comparative hybridization (for example, different fluorescent colors that must be read at two different wavelengths) and in particular, comparative genomic hybridization methods. Accordingly, provided is a method of performing comparative hybridization by comparing the amount of test and reference nucleic acids hybridized to a nucleic acid array, the amounts determined by detecting a signal from the hybridized nucleic acids which are labeled with the same detectable label. This method is applicable to comparative hybridization methods in general and to CGH in particular. Accordingly, reference to CGH where the test and reference nucleic acid is genomic nucleic acid should be understood to encompass methods where the test and reference nucleic acids are other than genomic nucleic acids. By the same token, it will be understood that the type of label used is not critical and that various labels described herein and known in the art and yet to be discovered may be used in this invention and that reference to a single type label (e.g. fluorescent label) in any of the embodiments of the invention disclosed herein should be understood to include such other types of labels.

In a preferred embodiment of the methods provided herein, CGH is performed using two samples of genomic nucleic acids; a test sample containing genomic nucleic acids, and a reference or control sample containing genomic nucleic acids with no known chromosomal or genetic abnormalities. The test sample and the reference sample are co-hybridized to a nucleic acid array that contains a plurality of nucleic acids or nucleic acid segments spotted onto a surface (such as a glass slide) at discrete locations. The array may contain target nucleic acid markers for certain known genetic mutations or disease states, or may represent (in aggregate) an entire chromosome, or the full chromosomal complement to obtain a genetic profile similar to karyotyping. In these approaches the detectable label may be attached to the test and reference nucleic acids before hybridization or after hybridization. In another approach, the detectable label may be attached to one of the test or reference nucleic acids before hybridization while the label is attached to the other of the test or reference nucleic acid after hybridization. The detectable label may be attached covalently or non-covalently such as by a ligand-receptor interaction or by hybridization between complementary nucleotide sequences.

In some embodiments of the methods provided herein, the test and reference samples are labeled with a detectable label; preferably the test and reference samples are labeled with the same detectable label; preferably the detectable label is a fluorochrome; preferably the detectable label is dCTP-Cy3. In certain aspects, methods are provided that allow for the use of a single label to determine the relative amount of test and reference nucleic acids hybridized to the array. This may be achieved by various approaches as disclosed herein.

In a variation of the "subtractive approach", the test and reference nucleic acids are labeled with the same detectable label, and co-hybridized to an array. As a first step, the total detectable signal on the array, which represents label linked to both the test sample and the reference sample nucleic acids hybridized to the array, is first positionally quantified. The array is then subjected to a condition or treatment that causes selective degradation and/or selective removal of either the hybridized test nucleic acid or the reference nucleic acid. The remaining signal representing nucleic acid that is not selectively removed or degraded is then positionally quantified. The next step includes using the results of the two reads to determine the amount of the hybridized nucleic acid that is subject to being selectively removed. In a preferred approach, the signal representing the nucleic acid that is linked to the label by the susceptible linker is determined by subtracting the remaining signal following selective removal from the total signal. The signal from the two samples thus determined can be used to identify differences between the test sample genomic nucleic acids and the reference sample genomic nucleic acids so as to detect chromosomal or genetic abnormalities associated with the test sample nucleic acid.

In one aspect, a method of determining differences between nucleic acid in a test sample and a reference sample is provided. The method involves amplifying nucleic acid sequence from the test sample nucleic acid and amplifying nucleic acid sequence from the reference sample nucleic acid, where one of the amplification reactions is conducted using dUTP and not dTTP and the other is conducted using dTTP and not dUTP; hybridizing to a nucleic acid array a solution comprising the amplified test sample and amplified reference sample; and determining the relative amount of hybridized test and reference nucleic acids bound to the array. In certain embodiments of the methods provided herein, determining the relative amount of hybridized test and reference nucleic acids includes a) determining a signal for the detectable label hybridized to the array representing the total of hybridized test and reference nucleic acid; b) treating the hybridized nucleic acids with an enzyme that selectively degrades DNA having uracil residues; and c) determining a signal for the detectable label hybridized to the array following step b), which signal represents one of the hybridized test or reference nucleic acid.

In particularly preferred embodiments of the methods provided herein, the enzyme that selectively degrades DNA having uracil residues is uracil-DNA N-glycosylase (UNG).

In another aspect, a method of determining differences between nucleic acid in a test sample and a reference sample is provided, where the method involves: (a) contacting under hybridization conditions a test sample containing nucleic acids and a reference sample containing nucleic acids to a surface containing a plurality of nucleic acid segments each immobilized at discrete locations on the surface, where the test sample and the reference sample are labeled before or after hybridization with the same detectable label; (b) determining the location and amount of the detectable label linked to nucleic acids hybridized to the surface; (c) selectively removing either the hybridized test sample nucleic acids or the hybridized reference sample nucleic acids; (d) determining the location and amount of the detectable label linked to nucleic acids hybridized to the surface following step (c); and (e) comparing the results of step (b) to the results of step (d) to detect differences in the nucleic acids of the test sample and reference sample.

In some preferred embodiments of the methods provided herein, the step of selectively removing hybridized test nucleic acids or reference nucleic acids is performed by subjecting the nucleic acids to an enzyme that selectively degrades DNA having certain properties; preferably an enzyme that degrades DNA having uracil residues; more preferably the enzyme that selectively degrades DNA having uracil residues is uracil-DNA N-glycosylase (UNG). In some embodiments of the methods provided herein, the step of selectively removing hybridized test nucleic acids or reference nucleic acids by subjecting nucleic acids to an enzyme that selectively degrades DNA having uracil residues is achieved by (1) amplifying sequence from a test sample and amplifying sequence from a reference sample nucleic acid, where one of the amplification reactions is conducted using dUTP and not dTTP and the other is conducted using dTTP and not dUTP; (2) hybridizing the amplified nucleic acids; and (3) treating the hybridized nucleic acids with an enzyme that selectively degrades DNA having uracil residues.

The methods provided herein may be used to detect any differences between nucleic acids in a test sample and a reference sample, including differences in the amount of nucleic acids having a particular sequence or differences in nucleic acid sequences. In particularly preferred embodiments, the methods are used to detect genetic abnormalities in the test sample. The methods provided herein may by applied to CGH using a chromosomal spread or array-based CGH. In some preferred embodiments, the methods provided may be used to compare the expression of genes in a test sample versus that of a reference sample.

In one aspect of the methods provided herein, a method of performing comparative hybridization is provided. The method includes comparing the amount of test and reference nucleic acids hybridized to a nucleic acid array, wherein the amount of hybridized test and reference nucleic acids is determined by detecting a signal from the hybridized nucleic acids which are labeled with the same detectable label. In one embodiment, the amount of hybridized test and reference nucleic acids are determined by: a) determining a signal for the detectable label hybridized to the array representing the total of hybridized test and reference nucleic acid; b) treating the hybridized nucleic acids to selectively remove one of the test or reference nucleic acids; c) determining a signal for the detectable label hybridized to the array following step b), which represents one of the hybridized test or reference nucleic acid; and d) determining a signal for the other of the hybridized test or reference by using the signal from c) and b).

In certain preferred embodiments of the methods provided herein, the step of amplifying sequence from a test sample and amplifying sequence from a reference sample involves amplifying genomic DNA in the samples is conducted using random priming such as is well known in the art. Alternatively, the step of amplifying sequence from a test sample and amplifying sequence from a reference sample may involve using RNA to generate cDNA and amplifying the cDNA using random priming and or amplifying specific sequences using particular primers. In certain preferred embodiments, the amplification reaction may be performed using one or more labeled nucleotides as a means to label the amplified nucleic acids with a detectable label; preferably both test and reference sample nucleic acids are amplified with the same labeled nucleotide; preferably the labeled nucleotide is dCTP-Cy3.

In another aspect, a method of comparing the expression of genes in a test sample versus that of a reference sample is provided. The method includes comparing the amount of cDNA prepared from mRNA of a test sample and cDNA prepared from mRNA of a reference sample hybridized to a nucleic acid array, the amount of hybridized test and reference cDNA determined by detecting a signal from the hybridized cDNA which is labeled with the same detectable label. The method involves amplifying nucleic acid sequence from cDNA prepared from RNA of the test sample and amplifying nucleic acid sequence from cDNA prepared from RNA of the reference sample, where one of the amplification reactions is conducted using dUTP and not dTTP and the other is conducted using dTTP and not dUTP; hybridizing to the nucleic acid array a solution comprising the amplified test sample and amplified reference sample; and determining the relative amount of hybridized test and reference nucleic acids bound to the array. In certain embodiments of the methods provided herein, determining the relative amount of hybridized test and reference nucleic acids includes a) determining a signal for the detectable label hybridized to the array representing the total of hybridized test and reference nucleic acid; b) treating the hybridized nucleic acids with an enzyme that selectively degrades DNA having uracil residues; and c) determining a signal for the detectable label hybridized to the array following step b), which signal represents one of the hybridized test or reference nucleic acid.

U.S. Patent Application Publication Number 2007/0122820, hereby incorporated by reference in its entirety, discloses CGH methods to detect genetic abnormalities including balanced translocations using probes to detect specific sequences. In one aspect, a method is provided in which the methods involving probes disclosed in the 2007/0122820 application are used in conjunction with the methods provided herein.

The term "tag" as used herein, refers to any physical molecule directly or indirectly associated with a nucleic acids of a sample such that substantially all individual nucleic acid segments of that sample can be marked, purified, or captured via the same tag. The tag may be a member of a specific binding pair such as a ligand-receptor or a pair of oligonucleotides with a complementary sequence. The tag entity interaction referred to herein is understood to be a specific binding pair such as a ligand/receptor binding pair or a pair oligonucleotides with a complementary sequence. A tag/entity combination should be chosen so that the it does not appreciably interact with the other tag entity combination that is used together in comparative hybridization. This allows one to identify hybridized test from the reference nucleic acid by the specific interaction associated with each tag/entity.

In a preferred embodiment, the tag includes a unique oligonucleotide "capture sequence," which refers to a sequence of nucleotides that is essentially unique to the assay. In this case, the reactive entity includes an oligonucleotide complementary to the unique oligonucleotide capture sequence associated with one sample of nucleic acid segments. Preferably, the reactive entity complementary oligonucleotide is in a dendrimeric construct to provide a multiplicity of the detectable label.

As used herein, specific binding pair members include antigen-antibody, biotin-avidin, hormone-receptor, receptor-ligand, enzyme-substrate, lgG-protein A, and the like.

As used herein, "nucleic acid" refers to segments or portions of DNA, cDNA, and/or RNA. Nucleic acid may be derived or obtained from an originally isolated nucleic acid sample from any source (e.g., isolated from, purified from, amplified from, cloned from, reverse transcribed from sample DNA or RNA) or may be synthesized de novo. Nucleic acid includes an oligonucleotide, nucleotide or polynucleotide, and fragments or portions thereof, and to DNA or RNA of genomic or synthetic origin that may be single or double stranded, and represent the sense or antisense strand.

"Genomic nucleic acid" refers to some or all of the DNA from the nucleus of a cell. In some embodiments, genomic DNA may include sequence from all or a portion of a single gene or from multiple genes, sequence from one or more chromosomes, or sequence from all chromosomes of a cell. In contrast, the term "total genomic nucleic acid" is used herein to refer to the full complement of DNA contained in the genome of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA. Genomic nucleic acid may be obtained from the nucleus of a cell, or recombinantly produced. Genomic DNA also may be transcribed from DNA or RNA isolated directly from a cell nucleus. PCR amplification also may be used. Methods of purifying DNA and/or RNA from a variety of samples are well-known in the art.

As used herein, "cDNA" refers to DNA which is copied from RNA. cDNA copied from mRNA does not include the various non-coding sequences characteristic of genomic DNA.

As used herein, "chromosomal abnormality" refers to any difference in the DNA sequence from a wild-type or normal cell. A chromosomal abnormality may reflect a difference between the full genetic complement of all chromosomes contained in an organism, or any portion thereof, as compared to a normal full genetic complement of all chromosome in that organism. For example, a chromosomal abnormality may include a change in chromosomal copy number (e.g. aneuploidy), or a portion thereof (e.g. deletions, amplifications); or a change in chromosomal structure (e.g., translocations, mutations). "Aneuploid cell" or "aneuploidy" as used herein, refers to a cell having an abnormal number of at least one chromosome in interphase. For example, a normal human cell contains a total of 46 chromosomes in interphase, or 2 copies of each of chromosomes 1 through 22, and 2 sex chromosomes (XX or XY). An abnormal chromosomal copy number is any number other than two of the normal chromosomal complement of two copies of chromosomes 1 through 22, and any combination other than two of the sex chromosomes X and Y.

As used herein, "genetic abnormality" refers to a chromosomal abnormality that is known to be associated with a particular disease condition (e.g., a specific gene mutation causing a dysfunctional protein directly causing a disease state). A chromosomal or genetic abnormality may be hereditary, i.e., passed from generation to generation.

A "sample" as used herein may be acquired from essentially any diseased or healthy organism, including humans, animals and plants, as well as cell cultures, recombinant cells, cell components and environmental sources. Samples may be from any animal, including by way of example and not limitation, humans, dogs, cats, sheep, cattle, and pigs. Samples can be a biological tissue, fluid or specimen. Samples may include, but are not limited to, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, urine, and the like. Samples may also be processed, such as sectioning of tissues, fractionation, purification, or cellular organelle separation.

A "test sample" comprises genomic nucleic acids typically from a patient or a cell population suspected of, or being screened for, nucleic acid containing a chromosomal or genetic abnormality. A "reference sample" comprises genomic nucleic acids typically from a normal individual or wild-type cell population with a normal genetic profile. A "test sample" or "reference sample" also may comprise mRNA from which cDNA can be made.

The genomic nucleic acids from the test and reference samples are contacted under hybridization conditions to a surface containing a plurality of nucleic acid segments, each immobilized at discrete locations on the surface. The term "hybridization" as used herein, refers to the pairing of substantially complementary nucleotide sequences (strands of nucleic acid) to form a duplex or heteroduplex through formation of hydrogen bonds between complementary base pairs. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

Genomic nucleic acids of the test sample may be linked to a detectable label via a first linkage. Genomic nucleic acids of the reference sample may be linked to the same detectable label via a second linkage.

A "detectable label" as used herein refers any moiety that generates a detectable signal by spectroscopic, photochemical, biochemical, immunochemical, electromagnetic, radiochemical, or chemical means, such as fluorescence, chemifluoresence, or chemiluminescence, or any other appropriate means. Preferred detectable labels include fluorescent dye molecules, or fluorophores, such as fluorescein, phycoerythrin, Cy3™, Cy5™, allophycocyanine, Texas Red, peridenin chlorophyll, cyanine, FAM, JOE, TAMRA, tandem conjugates such as phycoerythrin-Cy5™, and the like. Cy3™, and Cy5™ are commonly used together in two color detection systems. In single label CGH, Cy3™ is preferred over Cy5™. The detectable label may be linked by covalent or non-covalent means to nucleic acids. Alternatively, a detectable label may be linked such as by directly labeling a molecule that achieves binding to another nucleic acid via a ligand-receptor binding pair arrangement or other such specific recognition molecules.

A "linkage" of a detectable label as used herein, means that the label is physically associated with genomic nucleic acids in a sample. In one embodiment, either the first linkage or the second linkage is susceptible to selective removal. i.e., the linkage of one label but not the other is susceptible to cleavage or separation allowing the label to be separated from the nucleic acid. Examples of pairs of linkages (i.e., a differential linkage where one linker of the pair is susceptible to selective removal) include linkage via two different chemical linkers, two different oligonucleotides, or two different peptide sequences, wherein the chemical linkers, oligonucleotides or peptide sequences differ in susceptibility to temperature, pH hydrolysis, radiation (e.g., nucleotide stretches or chemical entities sensitive to ultraviolet radiation; e.g., photocleavable entities), oxidative conditions, atmospheric conditions (e.g., exposure to ozone), buffer conditions, hydrolysis by an external agent (e.g., an enzyme, such as a restriction endonuclease or a homing endonuclease), or chemical cleavage (e.g., linkers containing a diol that can be selectively cleaved using saturated aqueous $NaIO_4$ for 30-40 minutes, or linkers containing a disulfide that can be cleaved with dithiothreitol or any other appropriate reducing reagent, such as those available from Fidelity Systems, Inc. Gaithersburg, Md.).

By "susceptibility" is meant that the detectable label associated with the nucleic acids containing the susceptible linkage is physically dissociated from about 80% or more, preferably 90% or more, more preferably 95% or more of the member nucleic acids of that sample. Treatments that remove less than 95% can be tolerated especially when the deficiency in removal can be calculated and factored into the final results. Other differential linkages include different chemical coupling or physical interactions of the label with nucleic acids of either the test or reference sample in the labeling process. The nucleic acids of the sample(s) may be labeled before hybridization to the array, or after hybridization to the array. In all of these examples, a susceptible linkage is created to render the nucleic acids of one sample subject to selective removal of the label associated with the nucleic acids in that sample, following an initial read of the hybridization. Thus, the same label may be read at two time points: (i) to detect the signal from the detectable label of both the test and reference nucleic acids hybridized to the array; and (ii) to detect the signal from the nucleic acids hybridized to the array that do not have the label attached by a linker that is susceptible to the treatment. Subtraction of these two readings yields a value representing the hybridized nucleic acid that is labeled via the linkage that was resistant to the removal treatment.

In a one approach, the label may be non-covalently associated with the sample or reference nucleic acid, thus allowing the nucleic acids to first be hybridized to the target before the label is attached. In this case, a first unique oligonucleotide can be attached to either the test or reference sample nucleic acids, wherein this oligonucleotide contains a unique hybridization sequence and a recognition site for a restriction endonuclease, a homing endonuclease, or a rare-cutting endonuclease as is known in the art and commercially available, for example from Fermentas Life Sciences (e.g., I-SceI). The other of the nucleic acids is preferably linked to a second oligonucleotide that contains a different unique hybridization sequence but does not contain this recognition site. Both nucleic acids with the attached oligonucleotides are separately detected using another detectably labeled oligonucleotide which is complementary to one or the other hybridization sequence. Such detectably labeled complementary oligonucleotide may be a dendrimeric complex. Using this embodiment, following application of both labeled oligonucleotides to the hybridized array, label associated via the first unique oligonucleotide may then be selectively removed by contact with the endonuclease specific for the recognition site in the first unique oligonucleotide.

A "dendrimer" as used herein, is an artificially manufactured or synthesized polymeric molecule built up from branched units called monomers. In a preferred embodiment, the monomers are DNA molecules which associate by base pairing to assemble (see, e.g., U.S. Pat. Nos. 5,175,270; 5,484,904; and 5,487,973). Other monomers include, but are not limited to, primary amines (see, e.g., U.S. Pat. No. 5,530,092); polyamidoamines, polyethyleneimines, and polypropyleneimines (see, e.g., U.S. Pat. Nos. 5,393,797; 5,393,795; 5,560,929; and 5,387,617); peptides; and other nucleic acids. Various tags (e.g., an oligonucleotide) may be attached to a terminal end of a dendrimer polymer or may be incorporated into the internal structure of the dendrimer. Attachment includes covalent attachment (e.g., the 3' end of an oligonucleotide is covalently attached to a terminal end of a dendrimer branch) as well as non-covalent interactions (e.g., nucleic acid hybridization). By incorporating a multiplicity of labels into the dendrimer, hybridization signal intensity is dramatically enhanced.

According to yet a further aspect of the invention, there is provided a method of comparing the expression of genes in a test sample versus that of reference sample. The first step of the method includes contacting under hybridization conditions cDNA prepared from mRNA of a test sample and cDNA prepared from mRNA of a reference sample to a surface containing a plurality of nucleic acid segments each immobilized at discrete locations on the surface. In this case, the test sample cDNA and the reference sample cDNA are labeled before or after hybridization with the same detectable label which is linked to the cDNA of the test sample via a first linkage, and to the cDNA of the reference sample via a second linkage. Either the first linkage or the second linkage is susceptible to selective removal and the detectable label linked to nucleic acids hybridized to the surface determined. The location and amount of detectable label linked to nucleic acids hybridized the surface of the support is determined. The label is then selectively removed from either the hybridized test sample cDNA or the hybridized reference sample cDNA. The location and amount of the detectable label remaining on the support is then determined and represents one of the samples. The difference between the location and amount remaining after removal compared and the location and amount prior to removal represents the other of the samples. The relative amount of each sample nucleic acid hybridized to the array reflects the expression of genes in the test sample compared to the reference sample.

The term "expression array" refers to a collection of cDNA sequences representing the complement of mRNA present in a cell at a particular time. A cDNA expression array may be prepared by oligo dT priming or random priming with hexomers. The random primer oligos may have 5' ligatable ends. After priming and extension to produce cDNA, the ligatable ends of the cDNA are ligated to a capture sequence via a bridging oligo. cDNA with capture sequences may then be hybridized to a solid phase containing immobilized nucleic acid probe sequences. The capture sequence may be detected with an appropriate labeled reagent (e.g. labeled dendrimeric nucleic acid) with a single stranded segment(s) (a.k.a. tail(s)) for the capture sequence. Exemplary supplies and protocols for preparing an expression array are available from manufacturers, for example, Genisphere, Inc.

Any of the embodiments disclosed herein for comparative genomic hybridization may be used to detect a chromosomal abnormality or genetic abnormality in any patient including adults, children and neonates.

DETAILED DESCRIPTION OF THE INVENTION

In accordance with the present invention, there are provided improved methods of performing single label array-based comparative genomic hybridization (CGH) to detect a chromosomal abnormality in a test sample, or to diagnose a genetic abnormality in an individual. In particular, variations of the subtractive methods described in the '665 application are provided. CGH is a molecular cytogenetics approach that can be used to detect regions in a genome undergoing quantitative changes, e.g., gains or losses of sequence or copy numbers. CGH is especially useful in the analysis and diagnosis of cancer, and the analysis and diagnosis of genetic disorders, such as in prenatal diagnosis. CGH reactions are typically used to compare the genetic composition of an unknown test sample with a known normal reference sample.

Sources of Genomic Nucleic Acids

In one aspect, the methods of the present invention can be used to detect a chromosomal abnormality in a test sample. In a preferred embodiment, the test sample is obtained from a patient. In another preferred embodiment, the test sample contains cells, tissues or fluid obtained from a patient suspected of having a pathology or a condition associated with a chromosomal or genetic abnormality. The causality, diagnosis or prognosis of the pathology or condition may be associated with genetic defects, e.g., with genomic nucleic acid base substitutions, amplifications, deletions and/or translocations. The test sample may be suspected of containing cancerous cells or nucleic from such cells. Samples may include, but are not limited to, amniotic fluid, biopsies, blood, blood cells, bone marrow, cerebrospinal fluid, fecal samples, fine needle biopsy samples, peritoneal fluid, plasma, pleural fluid, saliva, semen, serum, sputum, tears, tissue or tissue homogenates, tissue culture media, urine, and the like. Samples may also be processed, such as sectioning of tissues, fractionation, purification, or cellular organelle separation.

Methods of isolating cell, tissue or fluid samples are well known to those of skill in the art and include, but are not limited to, aspirations, tissue sections, drawing of blood or other fluids, surgical or needle biopsies, and the like. Samples derived from a patient may include frozen sections or paraffin sections taken for histological purposes. The sample can also be derived from supernatants (of cell cultures), lysates of cells, cells from tissue culture in which it may be desirable to detect levels of mosaicisms, including chromosomal abnormalities and copy numbers.

In a preferred embodiment, a sample suspected of containing cancerous cells is obtained from a human patient. Samples can be derived from patients using well-known techniques such as venipuncture, lumbar puncture, fluid sample such as saliva or urine, tissue or needle biopsy, and the like. In a patient suspected of having a tumor containing cancerous cells, a sample may include a biopsy or surgical specimen of the tumor, including for example, a tumor biopsy, a fine needle aspirate, or a section from a resected tumor. A lavage specimen may be prepared from any region of interest with a saline wash, for example, cervix, bronchi, bladder, etc. A patient sample may also include exhaled air samples as taken with a breathalyzer or from a cough or sneeze. A biological sample may also be obtained from a cell or blood bank where tissue and/or blood are stored, or from an in vitro source, such as a culture of cells. Techniques for establishing a culture of cells for use as a sample source are well known to those of skill in the art.

In another aspect, the methods of the present invention can be used to detect a chromosomal or genetic abnormality in a fetus. Prenatal diagnosis of a fetus may be indicated for women at increased risk of carrying a fetus with chromosomal or genetic abnormalities. Risk factors are well known in the art, and include, for example, advanced maternal age, abnormal maternal serum markers in prenatal screening, chromosomal abnormalities in a previous child, a previous child with physical anomalies and unknown chromosomal status, parental chromosomal abnormality, and recurrent spontaneous abortions.

The invention methods can be used to perform prenatal diagnosis using any type of embryonic or fetal cell. Fetal cells can be obtained through the pregnant female, or from a sample of an embryo. Thus, fetal cells are present in amniotic fluid obtained by amniocentesis, chorionic villi aspirated by syringe, percutaneous umbilical blood, a fetal skin biopsy, a blastomere from a four-cell to eight-cell stage embryo (pre-implantation), or a trophectoderm sample from a blastocyst (pre-implantation or by uterine lavage). Body fluids with sufficient amounts of genomic nucleic acid also may be used.

The method of the present invention utilizes a first population of genomic nucleic acids obtained from the test sample, and a second population of genomic nucleic acids obtained from a reference sample. The reference sample may be any cells, tissues or fluid as provided herein, obtained from an individual, or any cell culture or tissue culture, that does not contain any genetic abnormality, i.e., that has a normal genetic complement of all chromosomes.

Association of Label with Genomic Nucleic Acids

The genomic nucleic acids of both the test sample and the reference sample are associated with the same detectable label, either prior to or subsequent to hybridization. In preferred embodiments, the label is detectable by optical means, and is most preferably a fluorescent label or fluorophore. The detectable label can be incorporated into, associated with or conjugated to a nucleic acid. The association between the nucleic acid and the detectable label can be covalent or non-covalent. According to the methods of the present invention, the same detectable label is used to label both the genomic nucleic acids of the test sample and the genomic nucleic acids of the reference sample. Label can be attached by spacer arms of various lengths to reduce potential steric hindrance or impact on other useful or desired properties. See, e.g., Mansfield, *Mol. Cell. Probes* 9:145-156, 1995.

Useful labels include, e.g., fluorescent dyes (e.g., Cy5™, Cy3™, FITC, rhodamine, lanthamide phosphors, Texas red), $^{32}P$, $^{35}S$, $^{3}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), calorimetric labels (e.g., colloidal gold), magnetic labels (e.g., Dynabeads™), biotin, dioxigenin, or haptens and proteins for which antisera or monoclonal antibodies are available. The label can be directly incorporated into the nucleic acid to be detected, or it can be attached to a probe (e.g., an oligonucleotide) or antibody that hybridizes or binds to the nucleic acid to be detected.

In preferred embodiments, the detectable label is a fluorophore. The term "fluorophore" as used herein refers to a molecule that absorbs a quantum of electromagnetic radiation at one wavelength, and emits one or more photons at a different, typically longer, wavelength in response. Suitable fluorescent moieties include the following fluorophores known in the art:

4-acetamido-4'-isothiocyanatostilbene-2,2'disulfonic acid, acridine and derivatives (acridine and acridine isothiocyanate), Alexa Fluor® 350, Alexa Fluor® 488, Alexa Fluor® 546, Alexa Fluor® 555, Alexa Fluor™ 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS) N-(4-anilino-1-naphthyl) maleimide, anthranilamide, Black Hole Quencher™ (BHQ™) dyes (Biosearch Technologies), BODIPY® R-6G, BOPIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (eosin and cosin isothiocyanate), erythrosin and derivatives (erythrosin B and erythrosin isothiocyanate), ethidium, fluorescein and derivatives(
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate (FITC)
hexachloro-6-carboxyfluorescein (HEX)
QFITC (XRITC)
tetrachlorofluorescein (TET)
fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY®35 (Molecular Probes), Reactive Red 4 (Cibacron® Brilliant Red 3B-A), rhodamine and derivatives:
6-carboxy-X-rhodamine (ROX)
6-carboxyrhodamine (R6G)
lissamine rhodamine B sulfonyl chloride
rhodamine (Rhod)
rhodamine B
rhodamine 123
rhodamine green
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA), tetramethyl rhodamine, tetramethyl rhodamine isothiocyanate (TRITC), riboflavin, rosolic acid, and terbium chelate derivatives.

Other fluorescent nucleotide analogs can be used, see, e.g., Jameson, *Meth. Enzymol.* 278:363-390, 1997; Zhu, *Nucl. Acids Res.* 22:3418-3422, 1994. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Detectable labels can be incorporated into nucleic acids by covalent or non-covalent means, e.g., by transcription, such as by random-primer labeling using Klenow polymerase, or nick translation, or, amplification, or equivalent as is known in the art. For example, in one aspect, a nucleoside base is conjugated to a detectable moiety, such as a fluorescent dye, e.g., Cy3™ or Cy5™, and then incorporated into genomic nucleic acids. Nucleic acids can be incorporated with Cy3™- or Cy5™-dCTP conjugates mixed with unlabeled dCTP.

In another aspect, when using PCR or nick translation to label nucleic acids, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu, *Nat. Biotechnol* 18:345-348, 2000.

Alternative non-covalent incorporation of label can be achieved using other methods known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulphur containing side chains of amino acids. See, e.g., U.S. Pat. Nos. 5,580,990; 5,714,327; and 5,985,566; and European Patent No. 0539466. Thus, this system provides a method of associating any detectable label with members of a nucleic acid population, either directly into a nucleic acid or peptide molecule associated thereto, or indirectly via a complementary nucleic acid molecule or other partner molecule.

Labeling with a detectable label also can include a nucleic acid attached to another biological molecule, such as a nucleic acid, e.g., an oligonucleotide, or a nucleic acid in the form of a stem-loop structure as a "molecular beacon" or an "aptamer beacon". Molecular beacons as detectable moieties are well known in the art; for example, Sokol (*Proc. Natl. Acad. Sci. USA* 95:11538-11543, 1998) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (*Biochemistry* 40:9387-9395, 2001), describing a molecular beacon comprised of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, *Anal. Biochem.* 294:126-131, 2001; Poddar, *Mol. Cell. Probes* 15:161-167, 2001; Kaboev, *Nucl. Acids Res.* 28:E94, 2000. Aptamer beacons can adopt two or more conformations, one of which allows ligand binding. A fluorescence-quenching pair is used to report changes in conformation induced by ligand binding. See also, e.g., Yamamoto, *Genes Cells* 5:389-396, 2000; Smirnov, *Biochemistry* 39:1462-1468, 2000.

In a preferred embodiment, genomic nucleic acids are labeled using an oligonucleotide linkage. The genomic nucleic acids are first digested into fragments with a restriction enzyme (e.g., AluI); fragments are then associated with a unique capture sequence using a bridging oligonucleotide. When properly designed, the unique fragment is positioned directly adjoining the end of a nucleic acid such that ligation can be used to obtain covalent linkage. Each fragment can then be labeled with a dendrimeric construct comprising an oligonucleotide which hybridizes to the unique capture sequence associated with each fragment. The fragments of two or more samples of nucleic acids can be labeled via a unique capture sequence associated with each respective sample. In an especially preferred embodiment, multiple copies of the detectable label are attached to a dendrimer to achieve signal amplification. Preferably, the use of a dendrimer in the methods of the present invention allows more than 10, 20, 50, 100, or 200 fluorophore molecules to be attached to the genomic acids. Labeling of the fragments can be prior to hybridization of two or more nucleic acid samples, or preferably following hybridization to maximize signal intensity.

Alternatively, the genomic nucleic acid may be labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label may also be attached via a second peptide (such as on a dendrimer construct as above) that interacts with the first peptide (e.g., S—S association).

In another embodiment, the genomic nucleic acid may be labeled via a peptide nucleic acid. The term "peptide nucleic acid" (or PNA) as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen et al., *Anticancer Drug Des.* 8:53 63, 1993).

Indirect labeling may be performed prior to or preferably, after hybridization to maximize signal intensity. In a preferred embodiment, the hybridized surface is contacted with a first complex containing a detectable label and a first entity, wherein the first complex selectively reacts with the nucleic acids of either the test sample or the reference sample; and either simultaneously or subsequently with a second complex containing the same detectable label and a second entity, wherein the second complex selectively reacts with the nucleic acids of the other sample. In one embodiment, the first complex or the second complex may comprise a differential linkage of the detectable label, such that one sample may be subjected to selective removal of the detectable label (i.e., a subtractive approach). Alternatively, in another embodiment, the first complex and the second complex do not comprise a differential linkage of the detectable label, but instead, are added one following the other (i.e., an additive approach).

In certain embodiments, isolated or purified molecules may be preferred. As used herein, the terms "isolated", "purified" or "substantially purified" refer to molecules, either nucleic acid or amino acid sequences, that are removed from their natural environment, isolated or separated, and are at least 60% free, preferably 75% free, and most preferably 90% free from other components with which they are naturally associated. An isolated molecule is therefore a substantially purified molecule.

Hybridization

The methods of the present invention can incorporate all known methods and means and variations thereof for carrying out comparative genomic hybridization, see, e.g., U.S. Pat. Nos. 6,197,501; 6,159,685; 5,976,790; 5,965,362; 5,856,097; 5,830,645; 5,721,098; 5,665,549; 5,635,351; Diago, *Am. J. Pathol.* 158:1623-1631, 2001; Theillet, *Bull. Cancer* 88:261-268, 2001; Werner, *Pharmacogenomics* 2:25-36, 2001; Jain, *Pharmacogenomics* 1:289-307, 2000.

Generally, nucleic acid hybridizations comprise the following major steps: (1) immobilization of target nucleic acids; (2) pre-hybridization treatment to increase accessibility of target DNA, and to reduce nonspecific binding; (3) hybridization of the mixture of nucleic acids to the nucleic acid on the solid surface; (4) post-hybridization washes to remove nucleic acid fragments not bound in the hybridization and (5) detection of the hybridized nucleic acid fragments. If indirect detection is used, an additional step of hybridization with the labeled agent (e.g. dendrimer) and washing is needed. The reagent used in each of these steps and their conditions for use vary depending on the particular application.

In some applications it is necessary to block the hybridization capacity of repetitive sequences. A number of methods for removing and/or disabling the hybridization capacity of repetitive sequences are known (see, e.g., WO 93/18186). For instance, bulk procedures can be used. In many genomes, including the human genome, a major portion of shared repetitive DNA is contained within a few families of highly repeated sequences such as Alu. These methods exploit the fact that hybridization rate of complementary sequences increases as their concentration increases. Thus, repetitive sequences, which are generally present at high concentration will become double stranded more rapidly than others following denaturation and incubation under hybridization conditions. The double stranded nucleic acids are then removed and the remainder used in hybridizations. Methods of separating single from double stranded sequences include using hydroxyapatite or immobilized complementary nucleic acids attached to a solid support, and the like. Alternatively, the partially hybridized mixture can be used and the double stranded sequences will be unable to hybridize to the target.

Alternatively, unlabeled sequences which are complementary to the sequences whose hybridization capacity is to be inhibited can be added to the hybridization mixture. This method can be used to inhibit hybridization of repetitive sequences as well as other sequences. For example, Cot-1 DNA can be used to selectively inhibit hybridization of repetitive sequences in a sample. To prepare Cot-1 DNA, DNA is extracted, sheared, denatured and renatured. Because highly repetitive sequences reanneal more quickly, the resulting hybrids are highly enriched for these sequences. The remaining single stranded (i.e., single copy sequences) is digested with S1 nuclease and the double stranded Cot-1 DNA is purified and used to block hybridization of repetitive sequences in a sample. Although Cot-1 DNA can be prepared as described above, it is also commercially available (BRL).

Hybridization conditions for nucleic acids in the methods of the present invention are well known in the art. Hybridization conditions may be high, moderate or low stringency conditions. Ideally, nucleic acids will hybridize only to complementary nucleic acids and will not hybridize to other non-complementary nucleic acids in the sample. The hybridization conditions can be varied to alter the degree of stringency in the hybridization and reduce background signals as is known in the art. For example, if the hybridization conditions are high stringency conditions, a nucleic acid will bind only to nucleic acid target sequences with a very high degree of complementarity. Low stringency hybridization conditions will allow for hybridization of sequences with some degree of sequence divergence. The hybridization conditions will vary depending on the biological sample, and the type and sequence of nucleic acids. One skilled in the art will know how to optimize the hybridization conditions to practice the methods of the present invention.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segment with a high frequency of complementary base sequences.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5× Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2× SSC, 0.2% SDS, at 65° C. Low stringency refers to conditions equivalent to hybridization in 10% formamide, 5× Denhardt's solution, 6×SSC, 0.2% SDS, followed by washing in 1×SSC, 0.2% SDS, at 50° C.

As used herein, the terms "complementary" or "complementarity" are used in reference to polynucleotides (i.e., a sequence of nucleotides such as an oligonucleotide or a target nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'". Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity between two sequences. There may be partial homology or complete homology. A partially homologous sequence is one that is less than 100% identical to another sequence. Preferably, homologous sequences have an overall identity of at least 70% or at least 75%, more preferably at least 80% or at least 85%, most preferably at least 90% or at least 95%.

As used herein, the term "$T_m$" is used in reference to the "melting temperature". The melting temperature is the temperature at which a sample of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41$ (% G+C), when a nucleic acid is in aqueous solution at 1 M NaCl (see, e.g., Anderson and Young, Quantitative Filter Hybridization, in Nucleic Acid Hybridization, 1985). Other references (e.g., Allawi and SantaLucia, *Biochemistry* 36:10581-94, 1997) include more sophisticated computations which take structural and environmental, as well as sequence characteristics into account for the calculation of $T_m$.

Uracil-DNA N-glycosylase

The enzyme uracil-DNA N-glycosylase (UNG) selectively degrades nucleic acid having uracil residues by removing the uracil base from the DNA backbone leading to degradation of the abasic DNA (both single- and double-stranded) upon subsequent heating or change in pH. Experimentally, UNG has been used to control contamination in PCR-based genotyping and sequencing applications as it can distinguish DNA incorporated with dUTP instead of dTTP and degrade those DNA molecules containing UTP. Accordingly, UNG degrades only DNA having uracil resides and does not degrade DNA having no uracil residues. Inventors have found that UNG is effective in degrading and selectively removing nucleic acid having uracil residues that are hybridized to an array without significantly affecting DNA hybridized to the array that does not have uracil residues (for example nucleic acid having thymine residues).

Arrays

Nucleic acids used in the methods of the present invention can be immobilized to or applied to an array or "biochip". The term "array" or "microarray" or "biochip" or "chip" as used herein refers to a plurality of elements arranged onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston, *Curr. Biol.* 8:R171-R174, 1998; Schummer, *Biotechniques* 23:1087-1092, 1997; Kern, *Biotechniques* 23:120-124, 1997; Solinas-Toldo, *Genes, Chromosomes & Cancer* 20:399-407, 1997; Bowtell, *Nature Genetics Supp.* 21:25-32, 1999. See also published U.S. Patent Applications Nos. 20010018642; 20010019827; 20010016322; 20010014449; 20010014448; 20010012537; 20010008765.

Arrays are generically a plurality of "target elements" or "spots," each target element containing a defined amount of one or more biological molecules, e.g., polypeptides, nucleic acid molecules, or probes, immobilized at discrete locations on a substrate surface. In preferred embodiments, the plurality of spots comprises nucleic acid segments, immobilized at preferably at least about 50, at least about 100, at least about 300, or at least about 500 discrete locations on the surface. The plurality may comprise multiple repeats of the same nucleic acid segments to produce, e.g., duplicate spots, triplicate spots, quadruplicate spots, quintuplicate spots, etc.

The resolution of array-based CGH is primarily dependent upon the number, size and map positions of the nucleic acid elements within the array, which are capable of spanning the entire genome. Each nucleic acid of interest to be immobilized may be contained within a nucleic acid vector (e.g., plasmids, cosmids. etc.), or an artificial chromosome, such as a bacterial artificial chromosome (BAC) or P-1 derived artificial chromosome as is known in the art, which are capable of incorporating large inserts of nucleic acid. Typically, bacterial artificial chromosomes, or BACs, which can each accommodate on average about 150 kilobases (kb) of cloned genomic DNA, are used in the production of the array. Preferably, each nucleic acid segment of interest is between about 1,000 (1 kB) and about 1,000,000 (1 MB) nucleotides in length, more preferably between about 100,000 (100 kB) and 300,000 (kB) nucleotides in length. Nucleic acid segments of interest may be chosen to span (i.e. collectively represent) the sequence of at least one chromosome, spaced at intervals along the chromosome (i.e. containing segments of chromosomal sequence) of about 3-4 megabases (MB), more preferably at intervals of about 2-3 megabases along the chromosome, most preferably at intervals of about 1-2 megabases along the chromosome. To represent the entire genomic complement, nucleic acid segments may be chosen to span all chromosomes at such intervals. Alternatively, selected genomic regions of interest, e.g., known mutational hotspots, may be selected from one or more chromosomes. Such genomic regions of interest may be nucleic acid segments associated with a chromosomal abnormality, a contiguous gene abnormality, a genetically linked disease or syndrome.

Typically, the immobilized nucleic acid molecules are contacted with a sample for specific binding, e.g., hybridization, between molecules in the sample and the array. Immobilized nucleic acids segments can contain sequences from specific messages (e.g., as cDNA libraries) or genes (e.g., genomic libraries), including, e.g., substantially all or a subsection of a chromosome or substantially all of a genome, including a human genome. Other target elements can contain reference sequences, such as positive and negative controls, and the like. The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like.

Each target element may comprise substantially the same nucleic acid sequences, or, a mixture of nucleic acids of different lengths and/or sequences. Thus, for example, a target element may contain more than one copy of a cloned piece of DNA, and each copy may be broken into fragments of different lengths, as described herein. The length and complexity of the nucleic acid fixed onto the array surface is not critical to the invention. The array can comprise nucleic acids immobilized on any substrate, e.g., a solid surface (e.g., nitrocellulose, glass, quartz, fused silica, plastics and the like). See, e.g., U.S. Pat. No. 6,063,338 describing multi-well platforms containing cycloolefin polymers if fluorescence is to be measured. Arrays used in the methods of the invention can comprise housing containing components for controlling humidity and temperature during the hybridization and wash reactions.

The CGH methods of the invention can be performed using any type of array. Commercially available CGH arrays or prepared slides for array printing include, for example, GeneChips™ from Affymetrix, Santa Clara, Calif.; Spectral Chip™ Mouse BAC Arrays and Spectral Chip™ Human BAC Arrays and other custom Arrays from Spectral Genomics, Houston, Tex.; Codelink™ Human Bioarrays from Amersham Biosciences (GE Healthcare); and UltraGap™ from Dow Corning, Elizabethtown, Ky. UltraGap™ slides used in accordance with the manufacturer's suggested protocol are preferred.

In a preferred embodiment, the surface comprises an array containing one, several or all of the human genomic nucleic acid segments provided in a compendium of bacterial artificial chromosomes (BACs) compiled by The BAC Resource Consortium, and referred to in the art by their RPI or CTB clone names, see Cheung et al., *Nature* 409:953-958, 2001. This compendium contains 7,600 cytogenetically defined landmarks on the draft sequence of the human genome (see McPherson et al., *Nature* 409:934-41, 2001). These landmarks are large-insert clones mapped to chromosome bands by fluorescence in situ hybridization, each containing a sequence tag that is positioned on the genomic sequence. These clones represent all 24 human chromosomes in about 1 Mb resolution. Sources of BAC genomic collections include the BACPAC Resources Center (CHORI—Children's Hospital Oakland Research Institute), ResGen (Research Genetics through Invitrogen) and The Sanger Center (UK).

Many methods for immobilizing nucleic acids on a variety of solid surfaces are known in the art. For instance, the solid surface may be a membrane, glass, plastic, or a bead. The desired component may be covalently bound or noncovalently attached through nonspecific binding. The immobilization of nucleic acids on solid surfaces is discussed more fully below.

A wide variety of organic and inorganic polymers, as well as other materials, both natural and synthetic, may be employed as the material for the solid surface Illustrative solid surfaces include nitrocellulose, nylon, glass, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface of a solid support for array printing, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface may be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff et al., *Anal. Biochem.* 164:336-344, 1987); Kemsky et al., *Nucl Acids Res.* 15:2891-2910, 1987). Modified nucleotides can be placed on the target using PCR primers containing the modified nucleotide, or by enzymatic end labeling with modified nucleotides.

Alternative surfaces include derivatized surfaces such as chemically coated glass slides. On example, is the CodeLink™ Activated Slide from Amersham Biosciences. These slides are coated with a novel 3-D surface chemistry comprised of a long-chain, hydrophilic polymer containing amine-reactive groups, to react with and covalently immobilize amine-modified DNA for microarrays. This polymer is covalently crosslinked to itself and to the surface of the slide and is designed to orient the immobilized DNA away from the surface of the slide to improve hybridization. Another such 3D slide is UltraGap™, sold by Dow Corning.

Use of membrane supports (e.g., nitrocellulose, nylon, polypropylene) for the nucleic acid arrays of the invention is advantageous because of well developed technology employing manual and robotic methods of arraying targets at relatively high element densities (e.g., up to 30-40/cm$^2$). In addition, such membranes are generally available and protocols and equipment for hybridization to membranes is well known. Many membrane materials, however, have considerable fluorescence emission, where fluorescent labels are used to detect hybridization.

To optimize a given assay format one of skill can determine sensitivity of fluorescence detection for different combinations of membrane type, fluorophore, excitation and emission bands, spot size and the like. In addition, low fluorescence background membranes have been described (see, e.g., Chu et al., *Electrophoresis* 13:105-114, 1992).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorophore and membranes can thus be determined. Serial dilutions of pairs of fluorophore in known relative proportions can also be analyzed to determine the accuracy with which fluorescence ratio measurements reflect actual fluorophore ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from about 1 mm diameter down to about 1 μm can be used with these materials. Small array members containing small amounts of concentrated target DNA are conveniently used for high complexity comparative hybridizations since the total amount of probe available for binding to each element will be limited. Thus, it is advantageous to have small array members that contain a small amount of concentrated target DNA so that the signal that is obtained is highly localized and bright. Such small array members are typically used in arrays with densities greater than 10$^4$/cm$^2$. Relatively simple approaches capable of quantitative fluorescent imaging of 1 cm$^2$ areas have been described that permit acquisition of data from a large number of members in a single image (see, e.g., Wittrup et al., *Cytometry* 16:206-213, 1994).

Covalent attachment of the target nucleic acids to glass or synthetic fused silica can be accomplished according to a number of known techniques. Such substrates provide a very low fluorescence substrate, and a highly efficient hybridization environment.

There are many possible approaches to coupling nucleic acids to glass that employ commercially available reagents. For instance, materials for preparation of silanized glass with a number of functional groups are commercially available or can be prepared using standard techniques. Alternatively, quartz cover slips, which have at least 10-fold lower auto fluorescence than glass, can be silanized.

The targets can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling, using e.g., protein A following standard protocols (see, e.g., Smith et al., *Science* 258:1122-1126, 1992). Biotin or digoxigenin end-labeled nucleic acids can be prepared according to standard techniques.

Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

Interpretation of Array-Based CGH

The copy number of particular nucleic acid sequences in a test sample and a reference sample are compared by hybridizing the samples to one or more target nucleic acid segments. The hybridization signal intensity, and the ratio of intensities, produced by the detectable label associated with each sample is determined. Typically, the greater the ratio of the signal intensities on a target nucleic acid segment, the greater the copy number ratio of sequences in the two samples that bind to that element. Thus comparison of the signal intensity ratios among target nucleic acid segments permits comparison of copy number ratios of different sequences in the genomic nucleic acids of the two samples.

In addition to labeling nucleic acids with fluorescent dyes, the invention can be practiced using any apparatus or methods to detect detectable labels associated with nucleic acids of a sample, an individual member of the nucleic acids of a sample, or an array-immobilized nucleic acid segment, or, any apparatus or methods to detect nucleic acids specifically hybridized to each other. Devices and methods for the detection of multiple fluorophores are well known in the art, see, e.g., U.S. Pat. Nos. 5,539,517; 6,049,380; 6,054,279; 6,055,325; and 6,294,331. Any known device or method, or variation thereof, can be used or adapted to practice the methods of the invention, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. Patent Application Nos. 20010018514; 20010007747; and published international patent applications Nos. WO0146467 A; WO9960163 A; WO0009650 A; WO0026412 A; WO0042222 A; WO0047600 A; and WO0101144 A.

For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ or Cy3™, which have lower photodestruction yields an array can be read in less than 5 seconds.

Charge-coupled devices, or CCDs, are used in microarray scanning systems, including practicing the methods of the invention. Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively a spectral image can be made using brightfield microscopy, see, e.g., U.S. Pat. No. 6,294,331.

A specific advantage of the methods of the present invention is that a single detectable label may be used. This eliminates the need to read and co-ordinate multiple colored fluorophores. Thus, signal intensity at the lower range is uniform and can readily be normalized, as opposed to having to account for differences in signal intensity amongst more than one fluorophore. Other advantages of the present invention's array-based CGH approach include the increased resolution by spanning across the entire genomic sequence of each chromosome and the increased sensitivity achieved as compared to traditional in situ chromosomal hybridization.

The methods of the invention further comprise data analysis, which can include the steps of determining, e.g., fluorescent intensity as a function of substrate position, removing "outliers" (data deviating from a predetermined statistical distribution), or calculating the relative binding affinity of the targets from the remaining data. The resulting data can be displayed as an image with color in each region varying according to the light emission or binding affinity between targets and probes. See, e.g., U.S. Pat. Nos. 5,324,633; 5,863, 504; and 6,045,996. The invention can also incorporate a device for detecting a labeled marker on a sample located on a support, see, e.g., U.S. Pat. No. 5,578,832.

The invention will now be described in greater detail by reference to the following non-limiting examples.

EXAMPLE 1

Preparation of a Genomic Nucleic Acid Array

A variety of microarray equipment (e.g., BioRobotics Microgrid and others; collectively "arrayers") are available for printing the nucleic acid material onto a plurality of discrete locations of a solid surface. Two specific surfaces were printed with native BAC DNA to establish a protocol for the specific application of large-insert clone microarray fabrication (e.g., BACs, PACs, cosmids).

Typical prior art arrayer installation and validation protocols assess the printing performance of an arrayer using either dye-only solutions or dye-oligo DNA solutions. These conditions do not reflect the fluid dynamics associated with large clone array manufacturing and hence are sub-optimal for generating printing parameters. The present example described herein establishes a simple and qualitative approach to validating arrayers and establishing printing parameters for large insert clone microarray fabrication.

A sample collection of the large insert DNA clones (BACs, PACs, cosmids) intended for printing was resuspended in a salt containing printing buffer (e.g., 50-150 mM sodium phosphate, pH 8-9) at a concentration of 75-100 ng/μl. The DNA was briefly fragmented using an ultrasonic water-bath processor set at 100 A with 70 W output for 5 seconds. Gel electrophoreses (0.8-1.0% agarose) was used to confirm that the size of the fragmented DNA ranged homogenously within 500 base pairs and larger. To a 30 μl aliquot of the sonicated DNA was added 1 μl of fluorescent nucleotide dye-conjugate (1 mM) of choice. Samples were mixed and transferred to a printing surface. Upon completion of the printing process, the resulting image was evaluated by scanning with a laser scanner (e.g., Axon 4000, 4100, 4200) set at the wavelength of fluorescent dye used.

Under these typical parameters, two surfaces were tested. The first surface was plain glass slides cleaned according to a standard base/acid protocol. Fluorescent measurements on plain glass slides indicated a background reading of about 3000, with a spot intensity of about 10,000, and a spot size of approximately 290 μm. The second surface was the CodeLink™ Activated Slide (Amersham Biosciences). Fluorescent measurements on the CodeLink™ Activated Slide indicated a background reading of about 15,000, with a spot intensity of about 65,000, and a spot size of approximately 180 μm.

EXAMPLE 2

Preparation of Genomic Nucleic Acids

Labeling. Genomic DNA may be labeled by any standard protocol to incorporate a detectable label. An exemplary random priming with a fluorophore is as follows. In a 100 μl reaction containing 1 ng to 1 μg DNA, combine 1× random primers solution (BioPrime DNA Labeling System, Gibco BRL), 1 mM Tris, pH 7.6, 0.1 mM EDTA, 0.2 mM each of dATP, dTTP and dGTP, 0.1 mM dCTP, 0.4 mM Cy3 or Cy5-dCTP (Amersham) and 160 U Klenow fragment (BioPrime DNA Labeling System, Gibco BRL). The DNA and random primers solution is incubated at 100° C. for 10 minutes in a total volume of 84 μl, prior to adding the other reagents, and then the final 100 μl reaction is incubated overnight at 37° C. Unincorporated nucleotides are removed using a Sephadex G-50 column.

Dendrimeric labeling. Genomic DNA may contain a tag contained within a dendrimeric construct. A dendrimer is a highly branched molecule created to integrate multiple copies of the desired detectable label to amplify detection. Kits for dendrimer labeling and construction are commercially available (e.g., Genisphere Inc.). Briefly, genomic DNA is digested with AluI to yield digested fragments of about 256 bp on average. The genomic DNA fragments are then treated with 3' TdT to attach a poly-T tail to each fragment. A ligation containing (i) a bridging oligonucleotide with a poly-A tail, (ii) a capture sequence oligonucleotide (with one end complementary to the bridging oligonucleotide), and (iii) the T-tailed fragments is then performed, resulting in each genomic DNA fragment having the same unique capture sequence at its 3' end. Each sample of genomic DNA (i.e., the test and the reference samples of nucleic acids) is coupled to a unique capture sequence prior to hybridization. Following hybridization, the genomic DNA fragments can then be labeled using a dendrimer that contains an oligonucleotide complementary to the unique capture sequence of a one sample and multiple copies of label, typically fluorescent dye molecules.

Alternatively, genomic mRNA is first reverse transcribed with unlabelled dATP, dTTP, dGTP and dCTP using a primer oligonucleotide that contains a unique capture sequence and a poly-T tail to hybridize to the poly-A tail of the mRNA molecules. The reaction is then stopped and the mRNA is degraded to yield genomic cDNAs containing the unique capture sequence. These genomic cDNAs can then be labeled using a dendrimer that contains an oligonucleotide complementary to the unique capture sequence and multiple copies of label, typically fluorescent dye molecules. Genisphere, Inc. offers a variety of dendrimers that vary in size and fluorescence intensity. The Array 900 and 350 series kits contain four-layer dendrimers. A four layer dendrimer theoretically has 324 single stranded DNA arms in the outer layer. The diameter of a four layer dendrimer is 182-190 nm and the molecular weight is $1.2 \times 10^7$ Daltons. The Array 50 series kit contains a two layer dendrimer. A two layer dendrimer theoretically has 45 single stranded DNA arms in the outer layer. The diameter of a two layer dendrimer is 70-90 nm and the molecular weight is $1.3 \times 10^6$ Daltons.

EXAMPLE 3

Comparative Genomic Hybridization

Genomic nucleic acids obtained from a test sample and a reference sample, each population containing a unique capture sequence, are combined (about 1-2 μg each) with Cot-1 DNA (80-100 μg) and precipitated with ethanol. Precipitate is collected by centrifugation and allowed to air dry for 10 minutes before re-dissolving it in a 50 μl hybridization mixture containing 50% formamide, 2×SSC, 10% dextran sulfate, 4% SDS and 500 μg yeast tRNA, pH 7. The hybridization mixture is incubated at 70° C. for 10-15 minutes to denature the DNA and subsequently at 37° C. for 60 minutes to allow blocking of repetitive sequences. To the array is added 50 μl of slide blocking solution containing 500 μg salmon sperm DNA in 50% formamide, 2×SSC, 10% dextran sulfate and 4% SDS, pH 7. After a 30 minute incubation at room temperature, approximately three-quarters of the blocking solution is removed, and the denatured and re-annealed hybridization mixture is added and hybridized at 37° C. for 16-72 hours. After hybridization, excess hybridization fluid is rinsed off with 0.1 M sodium phosphate, 0.1% NP40, pH 8, then the array is washed once in 50% formamide, 2×SSC, pH 7 at 45° C. for 15 minutes, and finally with 0.1 M sodium phosphate, 0.1% NP40, pH 8 at room temperature for 15 minutes.

EXAMPLE 4

Single Label CGH with Subtractive Labeling

An exemplary selective removal can be achieved by making the label associated with either the genomic nucleic acids obtained from the test sample or the genomic nucleic acids obtained from the reference sample susceptible to removal with atmospheric ozone. Certain fluorophores (e.g., Cy5™ and Alexa 647) are susceptible to ozone levels as low as about 5-10 ppm for periods as short as 10-30 seconds. Following hybridization, arrays are placed in an enclosed chamber with an ozone generator to achieve at atmospheric ozone level of about 60-85 ppm for about 10-30 minutes. Selective removal of the label from one population of genomic nucleic acids may be achieved by modifying the physical nature of the labeling process, such as increasing the distance of the label from the genomic DNA to increase exposure to the atmospheric ozone.

Another exemplary selective removal can be achieved by making the label associated with either the genomic nucleic acids obtained from the test sample or the genomic nucleic acids obtained from the reference sample susceptible to removal by cleavage with a restriction endonuclease or a homing endonuclease. In this example, reference sample genomic nucleic acids are prepared with a first unique capture sequence to which is linked a dendrimer containing an oligonucleotide complementary to this first unique capture sequence and a fluorescent label. The test sample genomic nucleic acids are prepared with a second unique capture sequence containing a stretch of nucleotides representing the recognition sequence for an endonuclease to which is linked a dendrimer containing an oligonucleotide complementary to this second unique capture sequence and the same fluorescent label as used for the first sample. Following hybridization of the test and reference genomic nucleic acids to an array containing a plurality of immobilized nucleic acid segments of interest, the fluorescence of the array is measured.

The array is then contacted with the endonuclease recognizing the sequence contained within the second unique capture sequence under conditions allowing cleavage of the dendrimeric construct from the genomic nucleic acids to selectively remove the fluorescent label from the test sample nucleic acids.

Another exemplary selective removal can be achieved by making the label associated with either the genomic nucleic acids obtained from the test sample or the genomic nucleic acids obtained from the reference sample susceptible to removal by UV irradiation. The label is incorporated using a linker that is photocleavable, such as a linker containing a 2-nitrobenzyl group (see, e.g., Bai et al., *Proc. Natl. Acad. Sci.* 100:409-413, 2003). Following hybridization, arrays are placed in a chamber with water and irradiated with a UV lamp at 340 nm (light intensity of about 20 mW/cm$^2$) for about 5-10 minutes to selectively remove the label from one population of genomic nucleic acids only (i.e., the nucleic acids containing the photocleavable linker).

Thus, in these examples of selective removal, data from the array is acquired at two time points, with the same fluorophore being read. The first acquisition is after the comparative genomic hybridization (e.g., before the selective removal of the label from the test sample genomic nucleic acids), in part to determine the fluorescence of the combined nucleic acid samples ($F_{Total}$). The second acquisition is after the selective removal of the label, in part to determine the remaining fluorescence of the reference sample genomic nucleic acids ($F_{Reference}$). The fluorescence of the test sample genomic nucleic acids ($F_{Test}$) is then equal to ($F_{Total} - F_{Reference}$). Thus, the same fluorophore can be used to achieve maximal uniformity between the two genomic nucleic acid samples, and between tests performed with different samples. If the selective removal is designed to remove nucleic acid associated with the reference genomic DNA, then the second read would be $F_{test}$ and the difference between $F_{Test}$ and $F_{Total}$ would be $F_{Reference}$.

As a quality control in single label CGH the two linkers for the test and reference labels are switched and comparative hybridization repeated.

EXAMPLE 5

Single Label CGH with Additive Labeling

Exemplary additive labeling for single label CGH can be achieved by performing a first comparative hybridization wherein the genomic nucleic acids obtained from the reference sample comprise a first unique oligonucleotide tag and the genomic nucleic acids obtained from the test sample comprise a second unique oligonucleotide tag. Following hybridization of the test and reference genomic nucleic acids to an array containing a plurality of immobilized nucleic acid segments of interest, the array is exposed to a first dendrimeric complex containing an oligonucleotide complementary to the first unique oligonucleotide tag and a fluorescent label. This provides a selective labeling of the reference sample genomic nucleic acids.

Preferred conditions for dendrimer hybridization include use of Pronto!™ hybridization buffer (Corning, Inc.) with 50 µg of Cot 1 DNA and 50-100 µg of SST (shredded (sonicated) salmon testis DNA). Cot 1 DNA may be replaced by any other non-mammalian genomic DNA such as plant DNA, fish DNA, bacterial DNA, and non-natural DNA, e.g. dendrimeric DNA. After 30 min. hybridization, the array is washed as follows:
1. Soak slide in 2×SSC containing 0.01% SDS (pH 7.5-8.0) at room temperature until coverslip is loosened (<3 minutes).
2. Incubate for 5 min. with gentle agitation at 50 C in 2×SSC containing 0.01% SDS (pH 7.5-8.0).
3. Incubate for 5 min. with gentle agitation at room temperature in 2×SSC (pH 7.5-8.0).
4. Incubate for 5 min. with gentle agitation at room temperature in 0.2×SSC (pH 7.5-8.0).
   SDS: sodium doedecyl sulfate (detergent)
   1×SSC: 0.15 molar sodium chloride and 0.015 molar sodium citrate Data from the array is then acquired, in part to determine the fluorescence of the first reference sample genomic nucleic acids ($F_{Reference}$). The array is then exposed to a second dendrimeric complex containing an oligonucleotide complementary to the second unique oligonucleotide tag and the same fluorescent label as used in the first dendrimeric complex. Data from the array is then acquired for a second time, in part to determine the fluorescence of the combined nucleic acids ($F_{Total}$). The fluorescence of the test sample genomic nucleic acids ($F_{Test}$) is then equal to ($F_{Total}-F_{Reference}$). Thus, the same fluorophore can be used to achieve maximal uniformity between the two genomic nucleic acid samples, and between tests performed with different samples. If the first dendrimeric complex binds to $F_{test}$, then the difference between $F_{Test}$ and $F_{Total}$ would be $F_{Reference}$.

As a quality control in single label CGH the unique tag sequences attached to the test and reference genomic nucleic acids are switched and comparative hybridization repeated.

EXAMPLE 6

Single Label CGH with Subtractive Labeling Using UNG

For the purposes of this example male genomic DNA was used as the "test sample" and female genomic DNA was used as the "reference sample."

Solution Preparation
dTTP Labeling Buffer: The following dNTPs were added to 47.3 mL of sterile water, 500 mL Tris-HCl pH 7.5, and 100 µL of 0.5M EDTA: 600 µL of 100 mM dATP, 300 µL of 100 mM dCTP, 600 µL of 100 mM dGTP and 600 µL of 100 mM dTTP.
dTTP Labeling Mix: 5 µL of dTTP Labeling Buffer was mixed with 1.0 µL Cy3-dCTP (Amersham Cat. # PA53031) and 1 µL exo-Klenow (Invitrogen Cat. # 18095-012).
dUTP Labeling Buffer: The following dNTPs were added to 47.3 mL of sterile water, 500 mL Tris-HCl pH 7.5, and 100 µL of 0.5M EDTA: 600 µL of 100 mM dATP, 300 µL of 100 mM dCTP, 600 µL of 100 mM dGTP and 600 µL of 100 mM dUTP.
dUTP Labeling Mix: 5 µL of dUTP Labeling Buffer was mixed with 1.0 µL Cy3-dCTP (Amersham Cat. # PA53031) and 1 µL exo-Klenow (Invitrogen Cat. # 18095-012).
Binding Buffer B2: (Invitrogen Cat. # K3100-2)
Wash Buffer W1: (Invitrogen Cat. # K3100-2)
UNG Digestion Solution: A volume of 3 µL of Uracil DNA glycosylase (UNG; Invitrogen Catalogue number 18054-015) and a volume of 3 µL of 10×PCR Buffer (Qiagen Cat. # 201203) were added to 24 µL sterile water.

Amplification Reaction

Test sample DNA and reference sample DNA (2 µg each) were diluted to final volumes of 22 µL and mixed gently. From the test sample DNA, 11 µL was aliquoted into a tube labeled "Test$_{dUTP}$" and 11 µL was aliquoted into a tube labeled "Test$_{dTTP}$"; and from the reference sample DNA, 11 µL was aliquoted into a tube labeled "Referenced$_{dUTP}$" and 11 µL was aliquoted into a tube labeled "Referenced$_{dTTP}$". Next, 12 µL of Random Primers (Invitrogen Cat. # 18095-012) were added to each of the "Test$_{dUTP}$"; "Test$_{dTTP}$"; "Reference$_{dUTP}$" and "Referenced$_{dTTP}$" tubes; the tubes were vortexed, centrifuged; denatured by heating 5 min at 99° C.; and then snap cooled on an ice slurry for 5 min.

Next, dTTP Labeling Mix (7 µL) was added to the "Test$_{dTTP}$" and "Referenced$_{dTTP}$" tubes; dUTP Labeling Mix (7 µL) was added to the "Test$_{dUTP}$" and "Reference$_{dUTP}$"; and the nucleic acids in the each of the tubes were amplified by incubating the tubes in the dark for 2 hours at 37° C. Next 3 µL of 0.5M EDTA was added to each of the amplifications reactions and the tubes were vortexed and centrifuged.

CGH Reactions

The amplified and labeled products of the "Test$_{dUTP}$" and "Referenced$_{dTTP}$" were combined and the amplified and labeled products of the "Test$_{dTTP}$" and "Reference$_{dUTP}$" were also combined.

The combined products were then purified using the PureLink PCR Purification System as follows: Binding Buffer B2 (400 µL) was added to each tube of the combined products; and the samples were loaded on to PureLink Spin 1 column; the columns were centrifuged ate 10,000 g for 1 min and the flow through was discarded; 650 µL of Wash Buffer W1 was added to each column; centrifuged ate 10,000 g for 1 min and the flow through was discarded; and the columns were re-centrifuged at high speed for an additional 2-3 minutes to remove any residual wash buffer. The columns were then transferred to Eppendorf tubes; 50 µL of sterile water was added to the columns and the columns were allowed to sit for 1 minute; the columns were centrifuged for 2 minutes at high speed and the flow through containing the purified combined nucleic acid products samples were saved.

The purified combined nucleic acid products were then precipitated to generate hybridization solutions as follows: 50 µg of human Cot-1 DNA and 100 µg of Salmon Sperm DNA were added to each of the solutions and the solutions were vortexed; a volume of 5M NaCl that was 1/12 of the total solution volume was added to each of the solutions and the solutions were vortexed; a volume of isopropanol that was 75% the total solution volume was added to each of the solutions and the solutions were vortexed; the solutions were left to sit at room temperature for 20 minutes and then centrifuged at high speed for 20 minutes; the supernatant was aspirated and the pellet was washed with 700 µL of 70% ethanol; the pellet was allowed to air-dry for 10 minutes; 20 µL of Pronto! Long Oligo Hybridization Solution (from Pronto! Universal Hybridization Kit) was added to each tube; the tubes were heated on a heat block at 95° C. for 2.5 minutes the tubes were vigorously vortexed for 15-30 seconds to dissolve the pellet and the tubes were placed back on the heating block at 95° for an additional 2.5 minutes; the tubes were vortexed vigorously and centrifuged at high speed for 2 minutes.

The precipitated hybridization samples were then hybridized to human BAC CGH arrays having 1296 clones printed in triplicate on aminosilane coated slides (Corning). Hybridization was performed as follows: 19 µL of the hybridization solutions were pippetted onto the individual arrays with the $Test_{dUTP}$/Referenced$_{dTTP}$ combined solution applied to the top array and the $Test_{dTTP}$/Reference$_{dTTP}$ applied to the bottom array; a cover slip was placed on each array to allow dispersion of the solution; 10 µl of de-ionized water was loaded onto each well of a hybridization chamber (Corning; catalog number 2551); the arrays were placed into the hybridization chamber and the chamber was sealed; the hybridization chambers were wrapped in foil; all components were sealed in a plastic bag with a moist paper towel; and the entire package was placed in a 42° C. incubator overnight. The next day the hybridized arrays were washed using standard genomic wash procedures and the arrays were baked at 80° C. for 30 minutes.

The hybridized arrays were then scanned using a an Axon 4200B scanner (Scan-1).

Following the scan the arrays were treated with UNG to selectively degrade and remove nucleic acids having uracil residues as follows: 30 µL of UNG Digestion Solution was pipetted onto the arrays; a LifterSlip (Fisher catalogue number 24X30I-2-5111-001-LS) was placed on the array to displace the solution; 10 µl of de-ionized water was loaded onto each well of a hybridization chamber (Corning; catalog number 2551); the arrays were placed into the hybridization chamber and the chamber was sealed; the hybridization chambers were wrapped in foil; the hybridization chambers were placed in a incubator at 37° C. for 1 hour; the hybridization chambers transferred to a 70° C. oven for 15 min; and the hybridized arrays were washed using standard genomic wash procedures.

Following the UNG treatment, the arrays were re-scanned using a an Axon 4200B scanner (Scan-2).

The array data for the CGH arrays were analyzed and calculated using Array CGH software developed by Info-Quant. Differences between the Test and Reference nucleic acids were calculated using the following formula for CGH where the reference nucleic acids were amplified with dTTP and test nucleic acids were amplified with dUTP: (Scan-1–Scan-2)/Scan-2=Test/Reference. Differences between the Test and Reference nucleic acids were calculated using the following formula for CGH where the reference nucleic acids were amplified with dUTP and test nucleic acids were amplified with dTTP: (Scan-1–Scan-2)/Scan-2=Reference/Test.

Effect of UNG on Nucleic Acid Hybridized to the Array. Reference nucleic acid was amplified and hybridized to arrays in accordance with the procedures described above in this example, with the exception that no test samples were used in the reaction. Specifically, reference DNA was amplified using dTTP and was amplified using dUTP. The amplified dUTP nucleic acid was applied to the top array and the dTTP nucleic acid was applied to the bottom array. The arrays were scanned, treated with UNG and then re-scanned. In the first scan, there was no significant difference between the reference DNA amplified using dTTP and that amplified using dUTP. In the second scan, the signal from the reference DNA amplified using dUTP was reduced to nearly undetectable levels indicating that the UNG had effectively degraded and removed from the array the uracil containing nucleic acids. In contrast to the DNA amplified using dUTP, in the array hybridized with reference nucleic amplified using dTTP there was no detectable difference in the signal from the first scan and the signal from the second scan performed after the UNG degradation. Accordingly, this example demonstrates that UNG is effective in selectively removing uracil containing uracil-containing nucleic acid from the array without having any significant effect on non-uracil-containing nucleic acid hybridized to the array.

Results of Single-Label UNG-Subtractive CGH Using Male and Female Genomic DNA. The results of CGH performed using normal male genomic DNA as a test sample and normal female genomic DNA a the reference sample as described in this example clearly demonstrated a loss of test (male) nucleic acid associated with the X-chromosome and an increase in nucleic acid associated with the Y-chromosome. There were no notable differences in the amount of nucleic acids associated with chromosomes other than the sex chromosomes.

EXAMPLE 7

Detection of a Chromosomal Deletion Using Single-Label UNG-Subtractive CGH

CGH was performed as described in Example 6 using genomic DNA from a female known to have a deletion in chromosome 3 (46,XX,del(3)(p12p21.1)) as the test sample and normal male genomic DNA as the reference sample. The results clearly demonstrated an increase of test nucleic acid associated with the X-chromosome and an decrease in nucleic acid associated with the Y-chromosome and in nucleic acid in the locus of the chromosome 3 where the known deletion was. There were no other notable differences in the amount of nucleic acids between the samples.

EXAMPLE 8

Detection of a Chromosomal Translocation Using Single-Label UNG-Subtractive CGH

CGH was performed as described in Example 6 using genomic DNA from a male known to have a translocation (ish XY,SubTel der(3)t(3p–;16q+)) as the test sample and normal female genomic DNA as the reference sample. The results clearly allowed for the detection of the translocation, i.e., the loss in both chromosome 3 and the gain in chromosome 16 in the test sample as compared to the reference sample, as well as the differences in the X and Y chromosomes. There were no other notable differences in the amount of nucleic acids between the samples.

EXAMPLE 9

Detection of a Chromosomal Deletion Using Single-Label UNG-Subtractive CGH

CGH was performed as described in Example 6 using genomic DNA from a male known to have a deletion in chromosome 11 (46,XY,del(11)(q23q23)) as the test sample and normal female genomic DNA as the reference sample. The results clearly allowed for the detection of the deletion, i.e., the loss of chromosome 11 in the test sample as compared to the reference sample, as well as the differences in the X and Y chromosomes. There were no other notable differences in the amount of nucleic acids between the samples.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method of determining a nucleotide sequence difference between nucleic acid in a test sample and nucleic acid in a reference sample, comprising:
    amplifying nucleic acid from a test sample and amplifying nucleic acid from a reference sample, wherein one of the amplification reactions is conducted using dUTP and not dTTP and the other is conducted using dTTP and not dUTP;
    hybridizing to a nucleic acid array a solution comprising the amplified test sample and amplified reference sample; and
    determining the relative amount of hybridized test and reference nucleic acids bound to the array, wherein a difference in the relative amount of hybridized test and reference nucleic acids bound to the array identifies the presence of a nucleotide sequence difference;
    wherein the sample amplified using dUTP is degraded.

2. The method of claim 1 wherein said amplified test sample is labeled with a detectable label.

3. The method of claim 1 wherein said amplified reference sample is labeled with a detectable label.

4. The method of claim 1 wherein said amplified test sample and said amplified reference sample are labeled with a detectable label.

5. The method of claim 4 wherein said amplified test and reference samples are labeled with the same detectable label.

6. The method of claim 1, wherein said test sample comprises genomic DNA.

7. The method of claim 1, wherein said test sample comprises cDNA.

8. The method of claim 5, wherein said detectable label is a flourochrome.

9. The method of claim 2, wherein said detectable label is dCTP-Cy3.

10. The method of claim 2, wherein said amplified nucleic acid is labeled with a detectable label by using a nucleotide labeled with a detectable label in the step of amplifying said test sample.

11. The method of claim 5, wherein said step of determining the relative amount of hybridized test and reference nucleic acids bound to the array comprises:
    a) determining a signal for the detectable label hybridized to the array representing the total of hybridized test and reference nucleic acid;
    b) treating the hybridized nucleic acids with an enzyme that selectively degrades DNA having uracil residues;
    c) determining a signal for the detectable label hybridized to the array following step b), which signal represents one of said hybridized test or reference nucleic acid; and
    d) determining a signal for the other of the hybridized test or reference by using the signal from a) and c).

12. The method of claim 11, wherein said enzyme that selectively degrades DNA having uracil residues is uracil-DNA N-glycosylase (LNG).

13. The method of claim 11, wherein said test sample is obtained from a patient.

14. The method of claim 11, wherein said test sample obtained from a patient is suspected of comprising cancerous cells.

15. The method of claim 11, wherein said test sample is obtained from a prenatal specimen.

16. The method of claim 11, wherein said test sample is obtained from an embryo or a fetus.

17. The method of claim 11, wherein said test sample is from an individual and the method is used to detect a genetic abnormality.

18. The method of claim 1, wherein said test sample comprises genomic nucleic acid.

19. The method of claim 1, wherein said step of determining the relative amount of hybridized test and reference nucleic acids bound to the array comprises:
    a) determining the amount of nucleic acids hybridized to the array representing the total of hybridized test and reference nucleic acid;
    b) treating the hybridized nucleic acids with an enzyme that selectively degrades DNA having uracil residues;
    c) determining the amount of nucleic acids hybridized to the array following step b), which represents one of said hybridized test or reference nucleic acid; and
    d) determining the amount of nucleic acids hybridized to the array for the other of the hybridized test or reference by using the results from a) and c).

20. The method of claim 19, wherein said enzyme that selectively degrades DNA having uracil residues is uracil-DNA N-glycosylase (UNG).

* * * * *

UNITED STATES PATENT AND TRADEMARK OFFICE
CERTIFICATE OF CORRECTION

| | | |
|---|---|---|
| PATENT NO. | : 7,892,743 B2 | |
| APPLICATION NO. | : 12/392951 | |
| DATED | : February 22, 2011 | |
| INVENTOR(S) | : Renius Owen and Charles M. Strom | |

It is certified that error appears in the above-identified patent and that said Letters Patent is hereby corrected as shown below:

Column 1, line 32, delete "Cancer" and replace with --CANCER--

Column 1, line 36, delete "chromosol al" and replace with --chromosomal--

Column 1, line 38, delete "18" and replace with --21--

Column 6, line 65, delete the word "the" after the word --that--

Column 8, line 53, delete "peridenin" and replace with --peridinin--

Column 15, line 18, delete the phrase "genomic acids" and replace with --genomic nucleic acids--

Column 15, line 40, delete the phrase "anti gene" and replace with --anti-gene--

Column 18, line 37, delete the word "resides" and replace with --residues--

Column 20, line 31, delete the "Mb" and replace with --MB--

Column 20, line 44, add a "." after the word --surface--

Column 26, 27, 28, and 29, words that are subscript should not be italicized

In claim 12, column 32, line 33 delete the word "LNG" and replace it with --UNG--

Signed and Sealed this
Twenty-fourth Day of May, 2011

David J. Kappos
*Director of the United States Patent and Trademark Office*